(12) United States Patent
Roye et al.

(10) Patent No.: US 11,555,692 B2
(45) Date of Patent: Jan. 17, 2023

(54) CALCULATION OF REDUNDANT BEND IN MULTI-CORE FIBER FOR SAFETY

(71) Applicant: Intuitive Surgical Operations, Inc., Sunnyvale, CA (US)

(72) Inventors: Patrick Roye, Christiansburg, VA (US); Mark E. Froggatt, Blacksburg, VA (US); Dawn K. Gifford, Blacksburg, VA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 43 days.

(21) Appl. No.: 17/184,357

(22) Filed: Feb. 24, 2021

(65) Prior Publication Data
US 2021/0187752 A1    Jun. 24, 2021

Related U.S. Application Data

(63) Continuation of application No. 16/315,773, filed as application No. PCT/US2017/038699 on Jun. 22, 2017, now Pat. No. 10,962,351.

(Continued)

(51) Int. Cl.
*B25J 9/00* (2006.01)
*B25J 9/12* (2006.01)
(Continued)

(52) U.S. Cl.
CPC ............ *G01B 11/161* (2013.01); *A61B 34/30* (2016.02); *A61B 34/35* (2016.02); *B25J 9/0096* (2013.01);
(Continued)

(58) Field of Classification Search
CPC ...... G01B 11/161; G01B 11/26; B25J 9/1694; A61B 2034/2061; A61B 2034/301
See application file for complete search history.

(56) References Cited

U.S. PATENT DOCUMENTS 6,471,710 B1   10/2002   Bucholtz
8,531,655 B2 *   9/2013   Klein ..................... G01L 1/242
                                                              356/73.1
(Continued)

FOREIGN PATENT DOCUMENTS

CN    103339467 A    10/2013
JP     5270174 B2     8/2013
(Continued)

OTHER PUBLICATIONS

International Preliminary Report on Patentability for Application No. PCT/US2017/038699, dated Jan. 17, 2019, 13 pages.
(Continued)

*Primary Examiner* — Shawn Decenzo
(74) *Attorney, Agent, or Firm* — Schwegman Lundberg & Woessner, P.A.

(57) ABSTRACT

A fiber includes M primary cores and N redundant cores, where M an integer is greater than two and N is an integer greater than one. Interferometric circuitry detects interferometric pattern data associated with the M primary cores and the N redundant cores when the optical fiber is placed into a sensing position. Data processing circuitry calculates a primary core fiber bend value for the M primary cores and a redundant core fiber bend value for the N redundant cores based on a predetermined geometry of the M primary cores and the N redundant cores in the fiber and detected interferometric pattern data associated with the M primary cores and the N redundant cores. The primary core fiber bend value and the redundant core fiber bend value are compared in a comparison. The detected data for the M primary cores is determined reliable or unreliable based on the comparison. A signal is generated in response to an unreliable determination.

20 Claims, 6 Drawing Sheets

Related U.S. Application Data

(60) Provisional application No. 62/359,716, filed on Jul. 8, 2016.

(51) Int. Cl.

| | | |
|---|---|---|
| *B25J 11/00* | (2006.01) | |
| *B25J 13/08* | (2006.01) | |
| *B25J 18/00* | (2006.01) | |
| *G01B 11/16* | (2006.01) | |
| *G01B 9/02004* | (2022.01) | |
| *A61B 34/30* | (2016.01) | |
| *A61B 34/35* | (2016.01) | |
| *B25J 9/16* | (2006.01) | |
| *G01B 11/26* | (2006.01) | |
| *A61B 34/20* | (2016.01) | |

(52) U.S. Cl.
CPC ............ *B25J 9/126* (2013.01); *B25J 9/1694* (2013.01); *B25J 11/005* (2013.01); *B25J 13/088* (2013.01); *B25J 18/00* (2013.01); *B25J 18/002* (2013.01); *G01B 9/02004* (2013.01); *G01B 11/26* (2013.01); *A61B 2034/2061* (2016.02); *A61B 2034/301* (2016.02)

(56) References Cited

U.S. PATENT DOCUMENTS

| | | | |
|---|---|---|---|
| 8,773,650 B2 | 7/2014 | Froggatt et al. | |
| 8,989,528 B2 | 3/2015 | Udd | |
| 10,132,614 B2 | 11/2018 | Froggatt et al. | |
| 10,962,351 B2 | 3/2021 | Roye et al. | |
| 2004/0165178 A1* | 8/2004 | Clements | G01L 1/242 |
| | | | 356/73.1 |
| 2006/0013523 A1 | 1/2006 | Childlers et al. | |
| 2007/0065077 A1 | 3/2007 | Childers et al. | |
| 2008/0212082 A1 | 9/2008 | Froggatt et al. | |
| 2011/0182557 A1 | 7/2011 | Hayashi | |
| 2012/0174883 A1 | 7/2012 | Kemnitz et al. | |
| 2013/0310685 A1* | 11/2013 | Chan | A61B 34/20 |
| | | | 600/424 |
| 2016/0101263 A1* | 4/2016 | Blumenkranz | A61B 5/6852 |
| | | | 600/117 |
| 2016/0157939 A1* | 6/2016 | Larkin | A61B 5/065 |
| | | | 600/424 |
| 2016/0206384 A1* | 7/2016 | Dimaio | A61B 34/20 |
| 2017/0370704 A1* | 12/2017 | Froggatt | G01L 1/242 |
| 2019/0029759 A1* | 1/2019 | McDonell | A61B 34/20 |
| 2019/0094459 A1* | 3/2019 | Froggatt | G02B 6/02 |
| 2019/0234726 A1* | 8/2019 | Gifford | G01D 5/35387 |
| 2019/0234727 A1 | 8/2019 | Roye et al. | |
| 2019/0250050 A1* | 8/2019 | Sanborn | G01B 11/18 |
| 2020/0069192 A1* | 3/2020 | Sanborn | A61B 5/1491 |
| 2020/0078096 A1* | 3/2020 | Barbagli | A61B 34/35 |
| 2020/0209466 A1* | 7/2020 | Sanborn | G02B 6/0238 |

FOREIGN PATENT DOCUMENTS

| | | |
|---|---|---|
| WO | WO-2015044930 A1 | 4/2015 |
| WO | WO-2015128761 A2 | 9/2015 |
| WO | WO-2017213874 A1 | 12/2017 |

OTHER PUBLICATIONS

Extended European Search Report for Application No. EP17824696.3 dated Dec. 10, 2019, 9 pages.

International Search Report and Written Opinion for Application No. PCT/US2017/038899, dated Oct. 27, 2017, 17 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

CALCULATION OF REDUNDANT BEND IN MULTI-CORE FIBER FOR SAFETY

This application is a continuation of and claims the benefit of priority under 35 U.S.C. § 120 to U.S. patent application Ser. No. 16/315,773, filed on Jan. 7, 2019, which is a U.S. National Stage Filing under 35 U.S.C. 371 from International Application No. PCT/US2017/038699, filed on Jun. 22, 2017, and published as WO 2018/009342 A1 on Jan. 11, 2018, which claims the benefit of priority under 35 U.S.C. § 119(e) to U.S. Provisional Patent Application No. 62/359,716, filed on Jul. 8, 2016, each of which is incorporated by reference herein in its entirety.

BACKGROUND

Multi-core optical fiber may be used to determine the bend angles of an optical fiber. A multi-core fiber having three cores can be used to separate the deformation of the fiber into two bend angles (pitch and yaw) and fiber elongation (strain).

In fiber optic based sensing of bend angles, a multi-channel distributed strain sensing system may be used to detect the change in strain for each of several cores within a multi-core optical bend sensing fiber as described for example in U.S. Pat. No. 8,773,650, incorporated herein by reference. Multiple distributed strain measurements may be combined through a system of equations to produce a set of physical measurements including curvature and axial strain a described in U.S. Pat. No. 8,531,655, incorporated herein by reference. These physical measurements may be used to determine distributed bend angles of the optical fiber.

Some applications for bend sensing fiber require a high degree of confidence or safety in terms of the accuracy and reliability of the bend sensing output. An example application is robotic arms used in surgical or other environments. One way of improving the confidence and safety in the operation of these robotic arms is to use redundancy. For example, rather than using just one position encoder to determine a current angular position of a robotic arm joint, two position encoders may be used and the outputs compared to determine if both encoders generating the same position or the same position with an allowed margin. If the outputs do not agree within the allowed margin, then a safety or fault signal may be generated to alert an operator of the error situation.

A redundant fiber may be an option for some bend sensing applications to ensure safe and reliable bend sensing output information. But in other situations, a redundant fiber may not be possible or desirable, e.g., due to space constraints, cost constraints, etc. For example, in surgical robotic arms, the conduit space that contains the bend sensing fiber may be too tight to accommodate two fibers. What is needed is another technological solution that ensures safe and reliable bend sensing output information but that does not require a redundant fiber.

SUMMARY

An interferometric measurement system measures an optical fiber including M primary cores and N redundant cores, where M is an integer is greater than two and N is an integer greater than one. (In one example implementation, M=3 and N=3, and in another, M=4 and N=2). Interferometric detection circuitry detects measurement interferometric pattern data associated with the M primary cores and the N redundant cores when the optical fiber is placed into a sensing position. Data processing circuitry calculates, based on a predetermined geometry of the M primary cores and the N redundant cores and detected measurement interferometric pattern data associated with the M primary cores and the N redundant cores, a primary core fiber bend value for the M primary cores and a redundant core fiber bend value for the N redundant cores. It also performs a comparison of the primary core fiber bend value and the redundant core fiber bend value, determines whether the detected measurement interferometric pattern data associated with the M primary cores is reliable or unreliable based on the comparison, and generates a signal in response to an unreliable determination.

In an example embodiment, the data processing circuitry determines that the detected measurement interferometric pattern data associated with the M primary cores is unreliable when a difference between the primary core fiber bend value and the redundant core fiber bend value exceeds a predetermined threshold.

The signal may represent one or more of the following: (a) an error in operation of optical and/or electronic sensing and processing circuitry, (b) an error in a connection with the optical fiber, (c) an error in calibration data determined for the optical fiber, (d) an error caused by a force experienced by the fiber that is otherwise not compensated for by the data processing circuitry, or (e) an error in processing or execution of algorithms resulting in miscalculation of the bend. The error can be a force caused by a pinch of the optical fiber and/or caused by one or more environmental conditions. The signal can also represent a reliability or an unreliability of the detected measurement interferometric pattern data associated with the M primary cores.

In a specific example, the data processing circuitry calculates a derivative of the phase measured in each of the M primary cores and the N redundant cores, and multiplies the phase derivatives for the M primary cores by a primary core conversion matrix and the phase derivatives for the N redundant cores by a redundant core conversion matrix.

In an example application the interferometric measurement system, when the optical fiber is inserted in a catheter of a robotic medical instrument having motor-operated movements, the data processing circuitry (1) determines that the detected measurement interferometric pattern data associated with the M primary cores is reliable based on the comparison, and (2) uses the reliable detected measurement interferometric pattern data associated with the M primary cores as feedback for actuating motors to move the robotic medical instrument to a particular shape or location.

In some example embodiments, the number M of primary cores is sufficient to determine twist or temperature associated with the fiber in addition to the primary core fiber bend value.

DETAILED DESCRIPTION

The following description sets forth specific details, such as particular embodiments for purposes of explanation and not limitation. But it will be appreciated by one skilled in the art that other embodiments may be employed apart from these specific details. In some instances, detailed descriptions of well-known methods, interfaces, circuits, and devices are omitted so as not to obscure the description with unnecessary detail. Individual blocks are shown in the figures corresponding to various nodes. Those skilled in the art will appreciate that the functions of those blocks may be implemented using individual hardware circuits, using software programs and data in conjunction with a suitably programmed digital microprocessor or general purpose computer, and/or using applications specific integrated circuitry (ASIC), and/or using one or more digital signal processors (DSPs). Software program instructions and data may be stored on a non-transitory, computer-readable storage medium, and when the instructions are executed by a computer or other suitable processor control, the computer or processor performs the functions associated with those instructions.

Overview

A multi-core optical fiber contains to a primary set of optical cores used to provide, in conjunction with an OFDR instrument, interferometric-based measurement of bend angles of the fiber. In example embodiments, the multi-core optical fiber also contains a second set of multiple cores for determining a redundant, interferometric-based measurement of the bend angles of the fiber. The redundant measurement of the fiber bend angles is compared to the primary measurement of the fiber bend angles in order to increase the confidence and reliability in the primary measurement. The redundant cores are located in different positions within the same multi-core fiber than the cores used in the primary measurement and detect errors caused by incorrect distributed strain measurements in any of the primary cores and errors caused by an incorrect mapping of distributed strain measurements to bend angles. In addition, since the additional cores require partially independent circuitry from the primary cores, any errors caused by the independent circuitry can also be detected.

Example multi-core fibers are described below for purposes of illustration and not limitation. The principles described also apply to a multi-core fiber where multiple primary cores and redundant cores have different relative positions along a length of the optical fiber. The technology applies to a spun fiber where the cores are helically wrapped in order to measure the twist on the fiber. The principles also apply to a multi-core fiber with more than six cores.

First Example Embodiment

Figure 1:
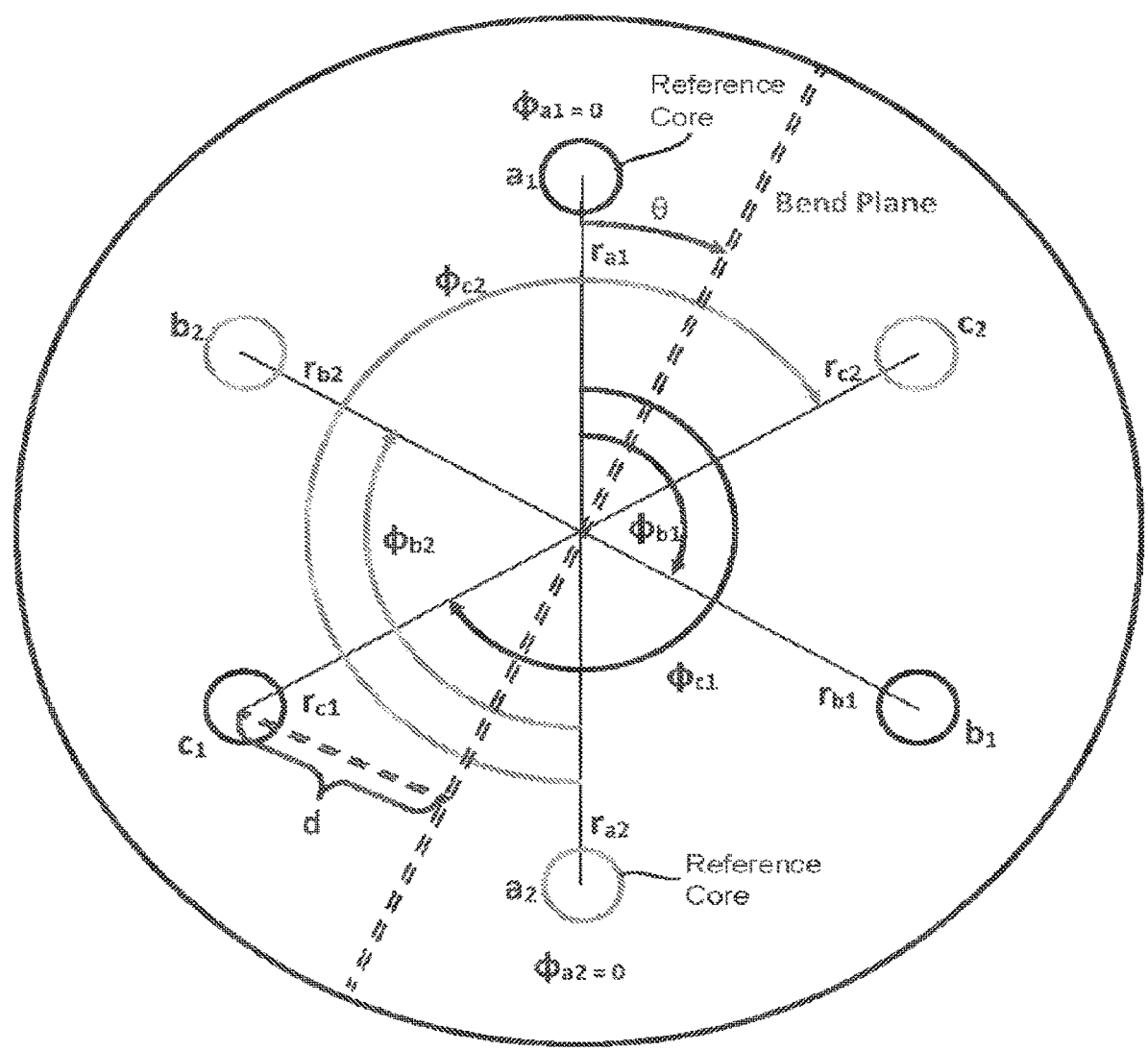
FIG. 1 illustrates mathematical parameters that can be used to quantify core placement and a response to strain for a six core optical fiber.

FIG. 1 shows a six core optical fiber along with mathematical parameters that can be used to quantify core placement and a response to strain. Although the term core is used, the technology applies to other types of waveguides that can be used in a fiber. Note that different numbers of cores may be used and that for simplicity all cores are at the same radius from the center of the multicore fiber. There are three primary measurement cores $a_1$, $b_1$, and $c_1$ and three redundant measurement cores $a_2$, $b_2$, and $c_2$. The number of primary measurement cores may be generalized to a positive integer M, and the number of redundant measurement cores may be generalized to a positive integer N. M and N may be the same as they are in FIG. 1, i.e., M=3 and N=3, or different as in FIG. 5, i.e., M=4 and N=2, described below.

A vertical axis through the center of the multi-core fiber passes through two of the outer or peripheral cores $a_1$ and $a_2$. These outer cores $a_1$ and $a_2$ are referred to as "reference cores" because several parameters are expressed relative to these cores $a_1$ and $a_2$. So core(s) identified herein with the letter "a" serve as one or more reference cores.

Two parameters describe the position of a core: the radial distance r from the fiber center, and an arbitrary angle 4 measured from the vertical axis intersecting the reference core(s). As the fiber is bent, the amount of bend-induced strain in a given core is directly proportional to the perpendicular distance d that the core is separated from the bend plane shown as a double-dashed line. This distance d is illustrated in FIG. 1 for the core $c_1$.

It is helpful to understand how these parameters impact the strain profile of the fiber when the core strain responses are used together to calculate the bend strain and axial strain applied to the fiber. A mathematical model is established based on the parameters shown in FIG. 1. Because these parameters can be measured, they can be used to provide a more accurate recombination of the strain profile of the multi-core optical fiber. It is notable that these parameters need only be measured once for a particular multi-core optical fiber and may be used for some or all OFDR subsequent measurements of that same multi-core optical fiber.

The bend strain B perceived by a core as a result of bending of the fiber is proportional to curvature of the bend and the tangential distance d of the core to the bend plane (shown in FIG. 1) in Equation (1) below:

$$B_n(z) = \alpha K(z) d_n(z) \quad (1)$$

in which α is a constant, K is the curvature of the fiber, and d represents the tangential distance of the core from the bend plane. From parameters shown in FIG. 1, the tangential distance d can be expressed in terms of the core's position as:

$$d_n(z) = r_n[\sin(\phi_n)\cos(\theta(z)) - \cos(\phi_n)\sin(\theta(z))] \quad (2)$$

in which r is the radial distance from the axis of the fiber, φ represents the angle measured from the vertical axis, and θ is a measure of the angle between the bend plane and the vertical axis. Combining equations (1) and (2) results in:

$$B_n(z) = \alpha K(z) r_n[\sin(\phi_n)\cos(\theta(z)) - \cos(\phi_n)\sin(\theta(z))] \quad (3)$$

This expression can be simplified by distributing the curvature term and expressing as two separate components:

$$B_n(z) = \alpha r_n[K_x(z)\sin(\phi_n) - K_y(z)\cos(\phi_n)] \quad (4)$$

in which $K_x$ is the curvature about the horizontal axis (pitch) and $K_y$ is the curvature about the vertical axis (yaw).

To a first order, it can also be assumed that the axial strain A experienced by the cores is common to all cores within the fiber and is not dependent on the position of the cores to arrive at the expression:

$$A_n(z) = \gamma E(z) \quad (5)$$

in which γ is a constant, and E represents axial strain. The total strain on a core can be written by combining equation (4) and equation (5) in the following expression:

$$\varepsilon_n(z) = \alpha r_n K_x(z)\sin(\phi_n) - \alpha r_n K_y(z)\cos(\phi_n) + \gamma E(z) \quad (6)$$

Considering the measured strain signals from the three primary cores in this example fiber embodiment, a matrix relationship can be constructed as follows:

$$\begin{bmatrix} \varepsilon_a(z) \\ \varepsilon_b(z) \\ \varepsilon_c(z) \end{bmatrix} = \begin{bmatrix} \alpha r_a \sin(\phi_a) & -\alpha r_a \cos(\phi_a) & \gamma \\ \alpha r_b \sin(\phi_b) & -\alpha r_b \cos(\phi_b) & \gamma \\ \alpha r_c \sin(\phi_c) & -\alpha r_c \cos(\phi_c) & \gamma \end{bmatrix} \begin{bmatrix} K_x(z) \\ K_y(z) \\ E(z) \end{bmatrix} \quad (7)$$

Equation (7) can be solved for the bend and strain parameters as follows:

$$\begin{bmatrix} K_{x1}(z) \\ K_{y1}(z) \\ E_1(z) \end{bmatrix} = \begin{bmatrix} \alpha r_{a1} \sin(\phi_{a1}) & -\alpha r_{a1} \cos(\phi_{a1}) & \gamma \\ \alpha r_{b1} \sin(\phi_{b1}) & -\alpha r_{b1} \cos(\phi_{b1}) & \gamma \\ \alpha r_{c1} \sin(\phi_{c1}) & -\alpha r_{c1} \cos(\phi_{c1}) & \gamma \end{bmatrix}^{-1} \begin{bmatrix} \varepsilon_{a1}(z) \\ \varepsilon_{b1}(z) \\ \varepsilon_{c1}(z) \end{bmatrix} \quad (8)$$

This expression in equation (8) allows recombination of individual strain signals of each independent core within the fiber, according to fiber structure variations, and sorting of these signals into strains that are applied to the entire multi-core fiber structure. Any number of linear combinations can be derived from equation (8) to create expressions that relate the strain response of a core to a component of the strain profile.

In a six core multi-core fiber example like that in FIG. 1, equation (8) can be applied twice to two independent triads of cores, i.e., the three primary measurement cores $a_1$, $b_1$, and $c_1$ and the three redundant measurement cores $a_2$, $b_2$, and $c_2$, shown in equation (9) and equation (10).

$$\begin{bmatrix} K_{x1}(z) \\ K_{y1}(z) \\ E_1(z) \end{bmatrix} = \begin{bmatrix} \alpha r_{a1} \sin(\phi_{a1}) & -\alpha r_{a1} \cos(\phi_{a1}) & \gamma \\ \alpha r_{b1} \sin(\phi_{b1}) & -\alpha r_{b1} \cos(\phi_{b1}) & \gamma \\ \alpha r_{c1} \sin(\phi_{c1}) & -\alpha r_{c1} \cos(\phi_{c1}) & \gamma \end{bmatrix}^{-1} \begin{bmatrix} \varepsilon_{a1}(z) \\ \varepsilon_{b1}(z) \\ \varepsilon_{c1}(z) \end{bmatrix} \quad (9)$$

$$\begin{bmatrix} K_{x2}(z) \\ K_{y2}(z) \\ E_2(z) \end{bmatrix} = \begin{bmatrix} \alpha r_{a2} \sin(\phi_{a2}) & -\alpha r_{a2} \cos(\phi_{a2}) & \gamma \\ \alpha r_{b2} \sin(\phi_{b2}) & -\alpha r_{b2} \cos(\phi_{b2}) & \gamma \\ \alpha r_{c2} \sin(\phi_{c2}) & -\alpha r_{c2} \cos(\phi_{c2}) & \gamma \end{bmatrix}^{-1} \begin{bmatrix} \varepsilon_{a2}(z) \\ \varepsilon_{b2}(z) \\ \varepsilon_{c2}(z) \end{bmatrix} \quad (10)$$

Since both the primary and redundant core triads experience the same global strains, the values $K_x$, $K_y$, and $E$ calculated for both triads should agree with one another. Any disagreement indicates an error in either the measurement or the assumptions underlying the measurement. In either case, the current measurement must be assumed to be flawed, and the bend and strain calculated must be considered unreliable and a potential hazard.

Figure 2:
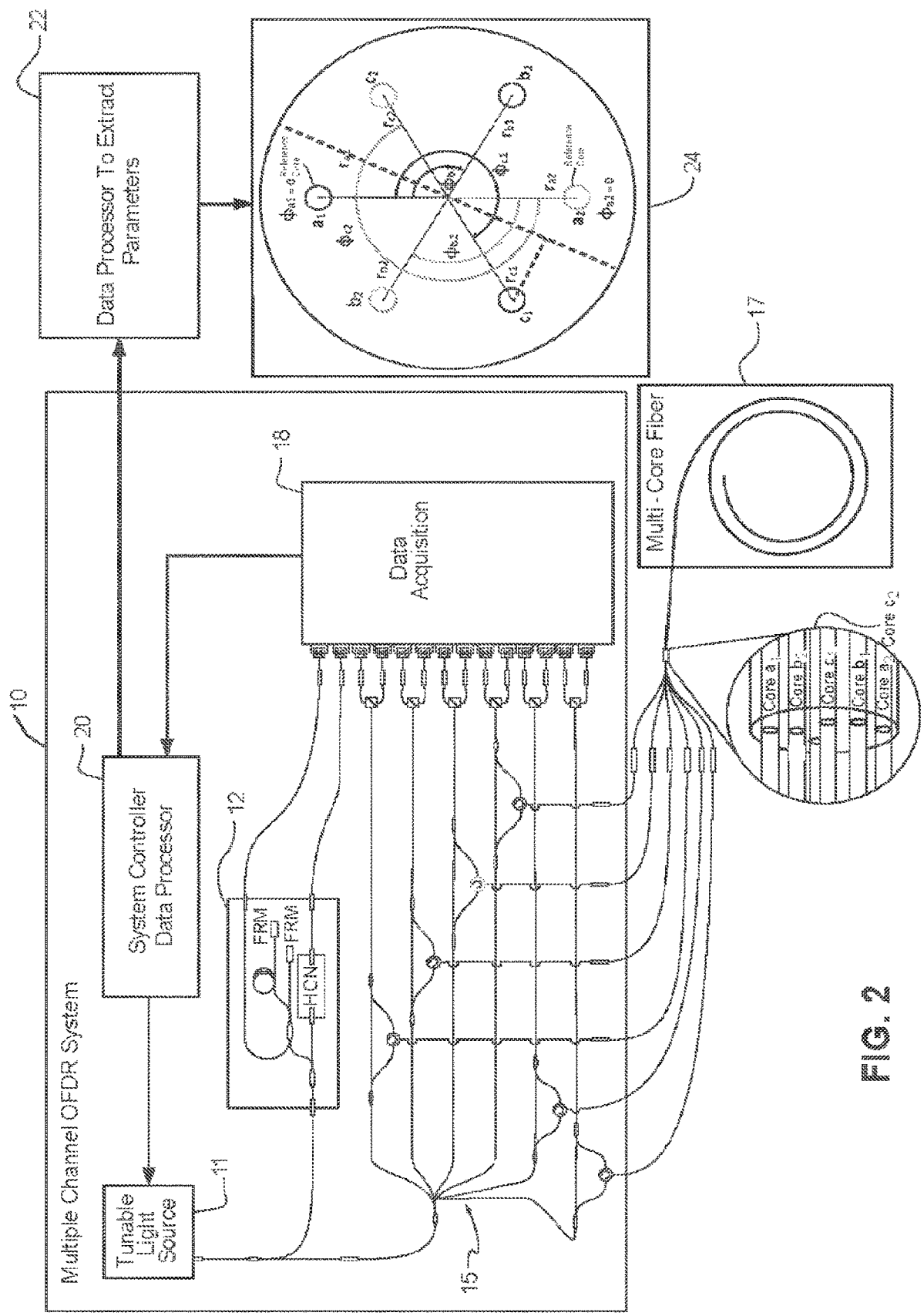
FIG. 2 shows a schematic diagram of a first example embodiment of an optical frequency domain reflectometry (OFDR)-based bend sensing system that identifies errors using a redundant measurement of the bend angles.

FIG. 2 shows a schematic diagram of an example embodiment of an optical frequency domain reflectometry (OFDR)-based bend sensing system 10 that uses a six core fiber like that in FIG. 1 to calculate redundant bend angles to detect measurement errors. The OFDR-based bend sensing system may be used to calculate redundant bend angles to detect measurement errors for other multicore fiber configurations.

An OFDR-based distributed strain sensing system 10 includes a light source 11, an interferometric interrogator 15, a laser monitor network 12, an optical fiber sensor 17, acquisition electronics 18, and a data processor 20. A single OFDR measurement and processing channel corresponds to one fiber core. During an OFDR measurement, a tunable light source 11 is swept through a range of optical frequencies. This light is split with the use of optical couplers and routed to separate interferometers. A reference interferometer is part of a laser monitor network 12 containing a Hydrogen Cyanide (HCN) gas cell that provides an absolute wavelength reference throughout the measurement scan. The reference interferometer within the laser monitor network 12 measures fluctuations in tuning rate as the light source 11 is scanned through a frequency range.

Measurement interferometric interrogators 15 are connected to respective individual cores in a length of multi-core bend sensing fiber 17. Light enters the sensing fiber 17 through the measurement arms of the six interferometric interrogators referenced generally at 15 corresponding to six core waveguides $a_1$-$c_1$ and $a_2$-$c_2$ in the fiber 17. Scattered light from each core in the sensing fiber 17 is then interfered with light that has traveled along the reference arm of the corresponding interferometric interrogator 15. Each pairing of an interferometric interrogator with a core in the multi-core fiber is referred to as an acquisition channel. As the tunable light source 11 is swept, each channel is simultaneously measured, and the resulting interference pattern from each channel is routed to the data acquisition electronics 18 adapted for the additional interferometers 15. Each channel is processed independently.

A series of optical detectors (e.g., photodiodes) convert the light signals from the laser monitor network, gas cell, and the interference patterns from each core from the sensing fiber to electrical signals. Processing circuitry in data acquisition unit 18 uses the information from the laser monitor 12 interferometer to resample the detected interference patterns of the sensing fiber 17 so that the patterns possess increments constant in optical frequency. This step is a mathematical requisite of the Fourier transform operation. Once resampled, a Fourier transform is performed by the system controller data processor 20 to produce a light scatter signal in the temporal domain. In the temporal domain, the amplitudes of the light scattering events are depicted against delay along the length of the fiber. Using the distance that light travels in a given increment of time, this delay can be converted to a measure of length along the sensing fiber. In other words, the light scatter signal indicates each scattering event as a function of distance along the fiber. The sampling period is referred to as the spatial resolution and is inversely proportional to the frequency range that the tunable light source 11 is swept through during the measurement.

As the fiber is strained, the local light scatters shift as the fiber changes in physical length. These distortions are highly repeatable. Hence, an OFDR measurement of detected light scatter for the fiber can be retained in memory that serves as a reference pattern of the fiber in an unstrained state. A subsequently measured scatter signal when the fiber is under strain may then be compared to this reference pattern by the system controller 20 to gain a measure of shift in delay of the local scatters along the length of the sensing fiber. This shift in delay manifests as a continuous, slowly varying optical phase signal when compared against the reference scatter pattern. The derivative of this optical phase signal is directly proportional to change in physical length of the sensing core. Change in physical length may be scaled to strain thereby producing a continuous measurement of strain along the sensing fiber.

The data processor 22 coupled to the system controller 20 extracts parameters 24 relating to the actual physical configuration of the cores $a_1$-$c_1$ and $a_2$-$c_2$ in fiber 17 that are used to calibrate or otherwise compensate the OFDR measurements to account for the variations between the actual optical core configuration and an optimal optical core configuration. The mathematical model described in detail above is first established that depicts parameters that describe variations from an optimal multi-core fiber configuration, where the term "optimal" includes known and unknown configurations. Calibration parameters are then defined that compensate for variation in the physical properties of the optical cores within the multi-core fiber.

Figure 3:
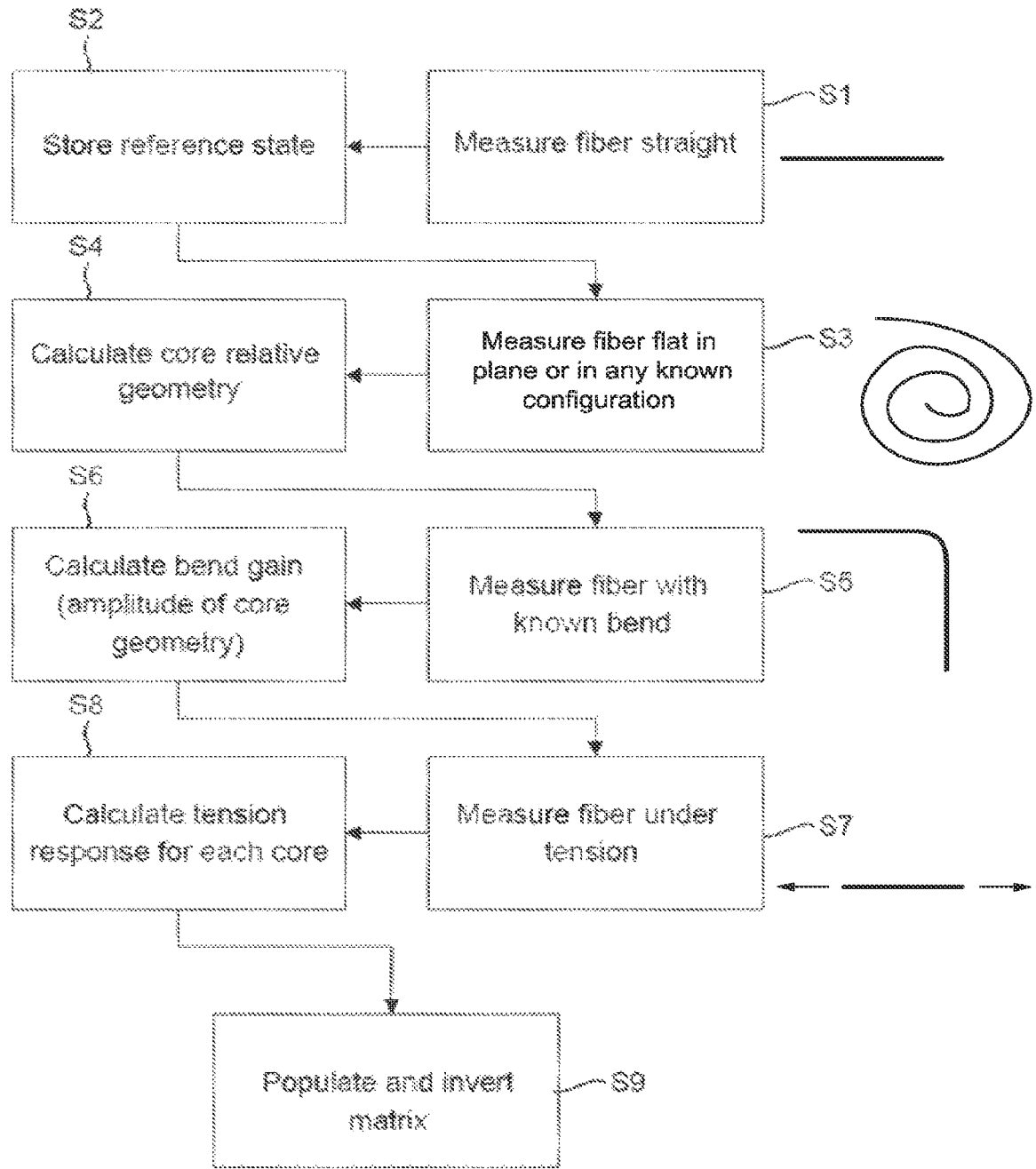
FIG. 3 is a flowchart diagram for calibrating the optical bend sensing fiber in the first example embodiment.

FIG. 3 is a flowchart diagram for calibrating a six core optical bend sensing fiber like that shown in FIG. 1. Initially, the multi-core fiber is placed in a straight line, unstrained configuration, and an OFDR measurement is performed (step S1) as described above, and the resulting reference state parameters are stored (step S2). The multi-core fiber is then configured in a known configuration such as in a flat plane, in a helical bend (e.g., a screw), or in any known configuration (step S3). In a non-limiting example, the multi-core fiber is configured in a flat plane (see the spiral shape shown to the right of step S3) to calculate the relative geometry between the cores in the fiber (step S4). The fiber is then configured into a known bend position (step S5), and a bend gain is calculated that provides amplitude values of the core geometry (step S6). The fiber is placed under tension (step S7), and a tension response for each core calculated (step S8). The values needed to populate the matrix in equation (8) above, which describes the response of the six cores to bend and strain are then determined, and the matrix is inverted (step S9).

Figure 4:
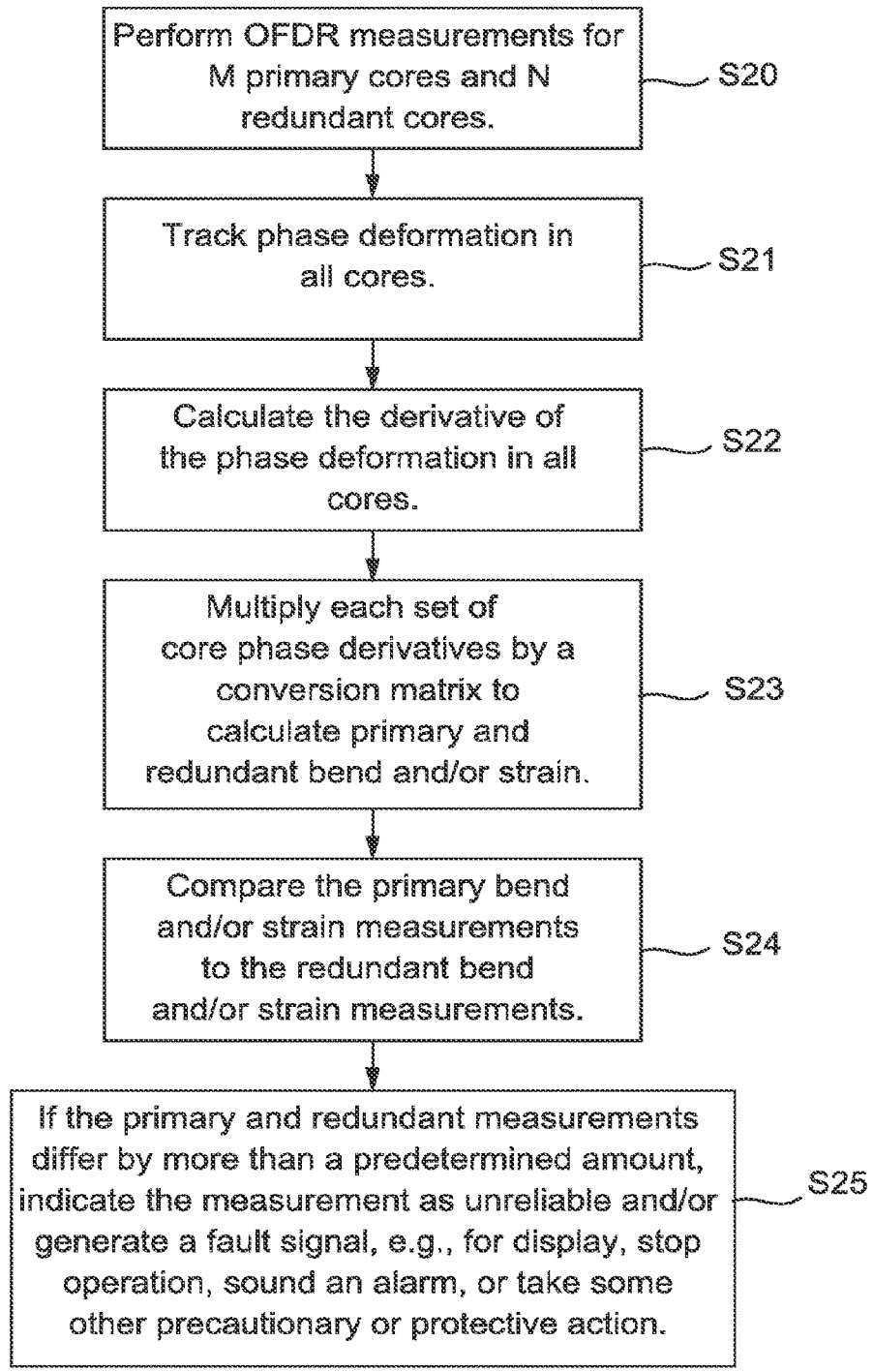
FIG. 4 is a flowchart diagram for detecting an error in bend sensing system of the first example embodiment.

FIG. 4 is a flowchart diagram, carried out by the system controller data processor 20 in example embodiments, for detecting an error in bend sensing system using a calibrated bend sensing fiber having M primary cores and N redundant. The flowchart process steps can be executed by any processor (e.g., FPGA, CPU, GPU, ASIC, etc.) including acquisition electronics 18 or data processor 22. Initially, the already-calibrated bend sensing fiber (e.g., see FIG. 3) is placed as desired for bend sensing, and OFDR measurements are obtained for each of the M+N cores (M primary cores and N redundant cores) (step S20). The data processor 22 tracks the optical phase signal for each core determined from these OFDR measurements as compared to the calibrated reference OFDR patterns for each corresponding core for this fiber as obtained for example following the example fiber calibration procedures from FIG. 3 (step S21). Each of the tracked optical phase signals is a measure of shift in delay of the reflections, e.g., local scatters or Bragg fiber grating reflections, along the length of its respective core in the sensing fiber. The derivative of this optical phase signal is calculated for each of the cores (step S22), which is directly proportional to change in physical length of its respective core. Each of the six phase derivatives is multiplied by the conversion matrix from equation (8) to determine the applied bend and strain (step S23).

Then the primary core OFDR measurements and redundant core OFDR measurements are compared to determine the reliability of the measurement (step S24). If the difference between the primary and redundant core OFDR measurements differ by more than a predetermined amount, then the OFDR measurements are labeled or otherwise indicated as unreliable and/or one or more the following actions is taken or initiated: generate a fault signal for display, stop operation of the system or machine associated with the bend sensing fiber, generate an alarm, and/or take some other precautionary or protection action (step S25).

Second Example Embodiment

The technology can also be applied to a multi-core fiber where more than three primary measurement cores are used. Additional primary measurement cores can be reused for the redundant bend calculation. This core configuration is useful for extracting additional parameters, such as the twist on the fiber or the temperature change along the fiber.

Figure 5:
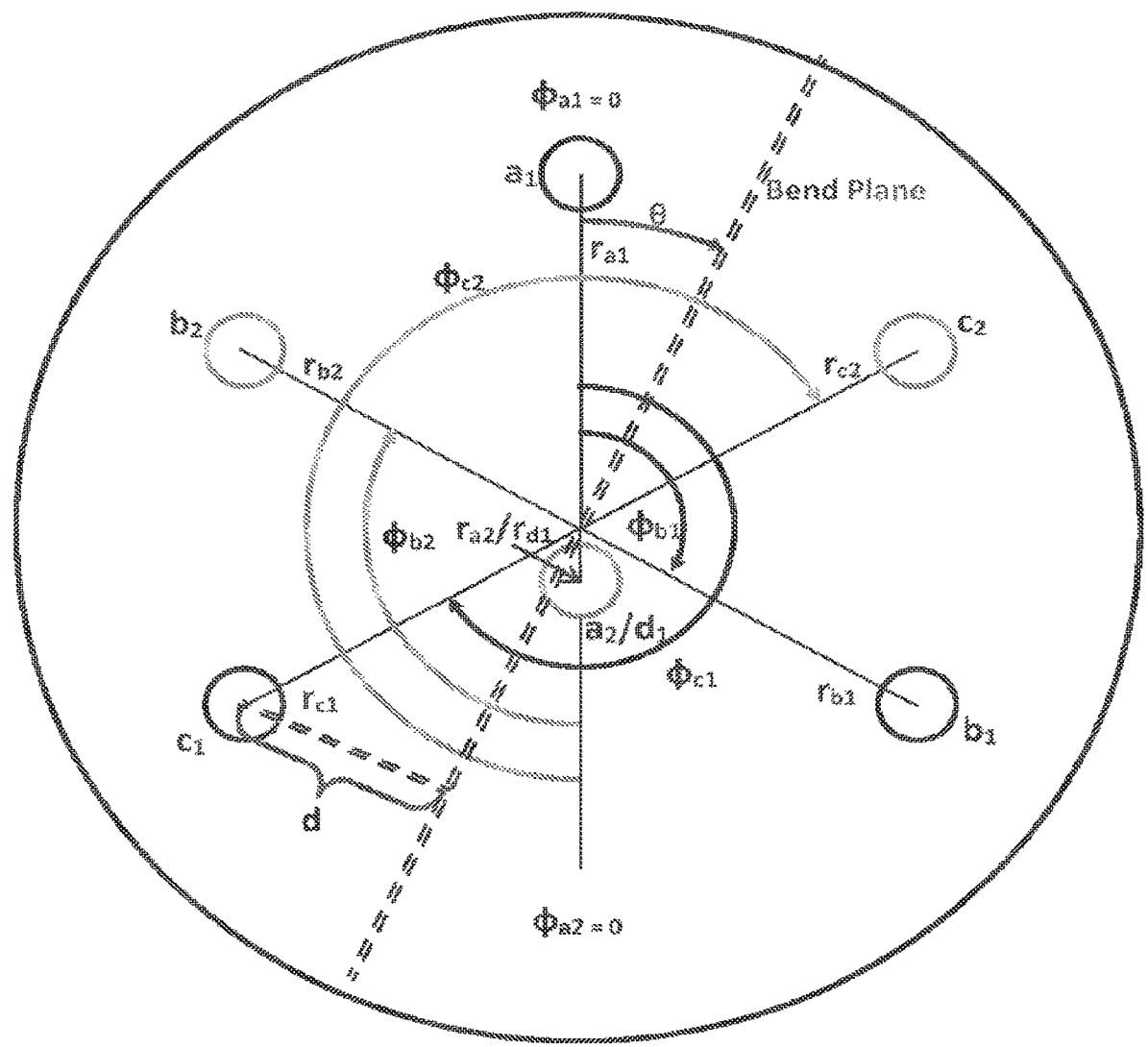
FIG. 5 illustrates mathematical parameters that can be used to quantify core placement and a response to strain for a six core optical fiber where one core is shared for primary and redundant calculations.

FIG. 5 illustrates mathematical parameters that can be used to quantify core placement and a response to strain for a six core optical fiber. In this example embodiment, core di is included as one of the primary cores in order to calculate the twist on a helical multi-core fiber, one example of which is described in U.S. provisional patent application Ser. No. 62/347,704, filed on Jun. 9, 2016, which is incorporated herein by reference. The same core is also used as a redundant core $a_2$. Thus, in this example, M=4 and N=2.

The inclusion of core di in the primary calculation allows the twist on the fiber to be calculated. For moderate levels of twist applied to a fiber (e.g., 100 degrees/meter), a first order term can be used to model strain induced by torque. Twist strain $R_n(z)$ is then expressed in terms of the core position as follows:

$$R_n(z) = \beta r_n^2 \Phi(z) \qquad (11)$$

in which β is a constant, and Φ is the amount the fiber has twisted (roll), per unit of length. The total strain on a core can be written by combining equation (4), equation (5), and equation (11) in the following expression:

$$\varepsilon_n(z) = \alpha r_n K_x(z)\sin(\phi_n) - \alpha r_n K_y(z)\cos(\phi_n) + \gamma E(z) + \beta r_n^2 \Phi(z) \qquad (12)$$

Considering the measured strain signals from the four primary cores in this example embodiment, a matrix relationship can be constructed as follows:

$$\begin{bmatrix} \varepsilon_{a1}(z) \\ \varepsilon_{b1}(z) \\ \varepsilon_{c1}(z) \\ \varepsilon_{d1}(z) \end{bmatrix} = \begin{bmatrix} \alpha r_a \sin(\phi_a) & -\alpha r_a \cos(\phi_a) & \gamma & \beta r_{a1}^2 \\ \alpha r_b \sin(\phi_b) & -\alpha r_b \cos(\phi_b) & \gamma & \beta r_{b1}^2 \\ \alpha r_c \sin(\phi_c) & -\alpha r_c \cos(\phi_c) & \gamma & \beta r_{c1}^2 \\ \alpha r_d \sin(\phi_d) & -\alpha r_d \cos(\phi_d) & \gamma & \beta r_{d1}^2 \end{bmatrix} \begin{bmatrix} K_{x1}(z) \\ K_{y1}(z) \\ E_1(z) \\ \Phi_1(z) \end{bmatrix} \qquad (13)$$

Equation (13) can be solved for the bend ($K_x$, $K_y$), strain (E), and twist (Φ) parameters as follows:

$$\begin{bmatrix} K_{x1}(z) \\ K_{y1}(z) \\ E_1(z) \\ \Phi_1(z) \end{bmatrix} = \begin{bmatrix} \alpha r_a \sin(\phi_a) & -\alpha r_a \cos(\phi_a) & \gamma & \beta r_{a1}^2 \\ \alpha r_b \sin(\phi_b) & -\alpha r_b \cos(\phi_b) & \gamma & \beta r_{b1}^2 \\ \alpha r_c \sin(\phi_c) & -\alpha r_c \cos(\phi_c) & \gamma & \beta r_{c1}^2 \\ \alpha r_d \sin(\phi_d) & -\alpha r_d \cos(\phi_d) & \gamma & \beta r_{d1}^2 \end{bmatrix}^{-1} \begin{bmatrix} \varepsilon_{a1}(z) \\ \varepsilon_{b1}(z) \\ \varepsilon_{c1}(z) \\ \varepsilon_{d1}(z) \end{bmatrix} \qquad (14)$$

This expression in equation (14) allows recombination of individual strain signals of each independent core within the fiber, according to fiber structure variations, and sorting of these signals into strains that are applied to the entire multi-core fiber structure. Any number of linear combinations can be derived from equation (14) to create expressions that relate the strain response of a core to a component of the strain profile.

The redundant bend calculation for this embodiment can be calculated using equation (10). Since both the primary and redundant cores experience the same global strains, the values $K_x$, $K_y$, and E calculated for both the primary and redundant cores should agree with one another. Any disagreement indicates an error in either the primary core OFDR measurements or the assumptions underlying the measurements. In either case, the current primary core OFDR measurements should be assumed flawed, and the bend and strain calculated therefrom considered unreliable and a potential hazard.

Figure 6:
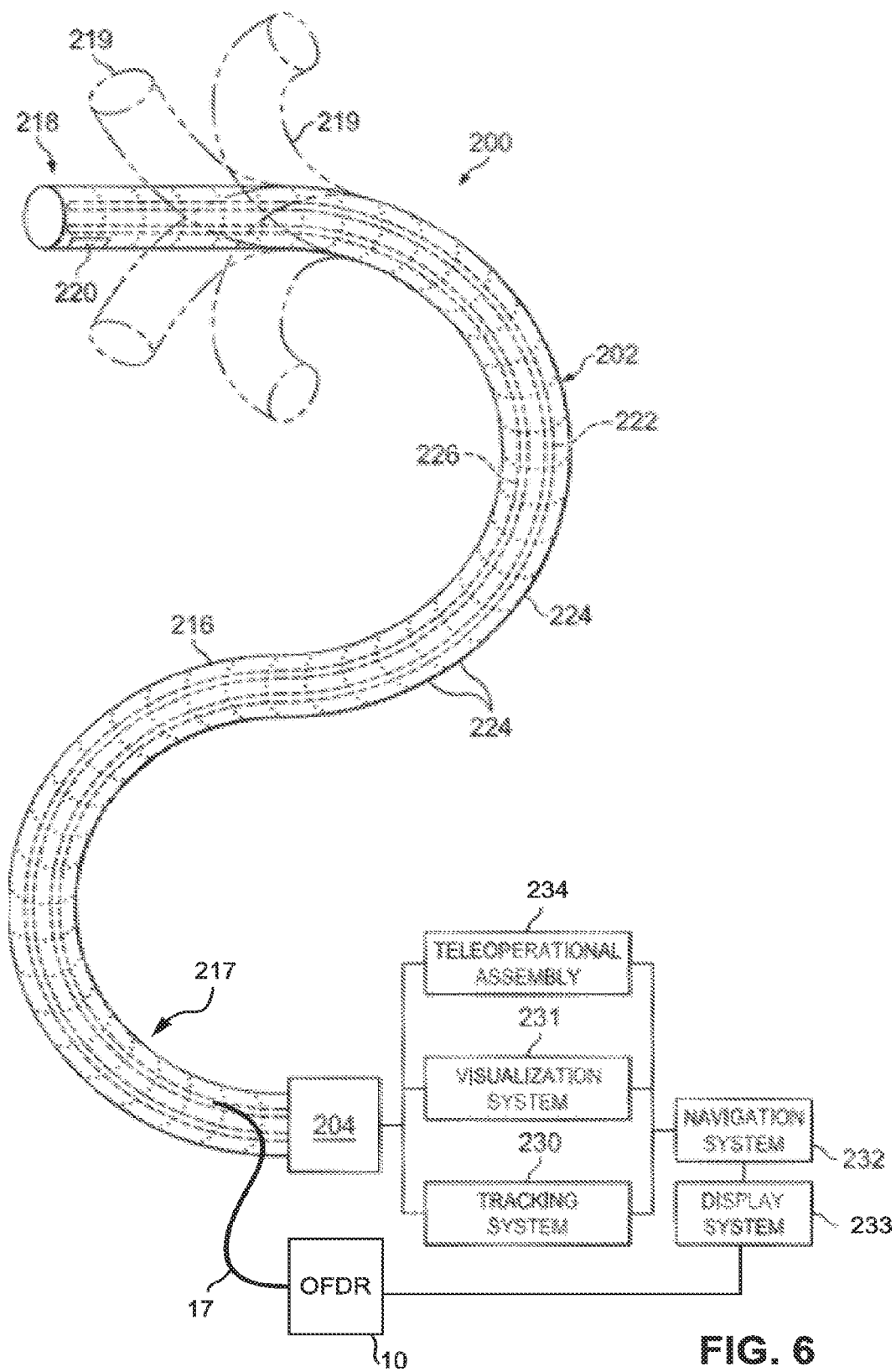
FIG. 6 shows an example application of the disclosed technology in a surgical robotic instrument.

FIG. 6 is a simplified diagram of a medical instrument system 200 according to example embodiments that benefits from the technology described above. In some embodiments, medical instrument system 200 may be used in an image-guided medical procedure performed with teleoperated medical system. In some examples, medical instrument system 200 may be used for non-teleoperational exploratory procedures or in procedures involving traditional manually operated medical instruments, such as endoscopy. Optionally, medical instrument system 200 may be used to gather (i.e., measure) a set of data points corresponding to locations within anatomic passageways of a patient.

Medical instrument system 200 includes elongate device 202 coupled to a motor drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of a catheter tip at distal end 218 and/or of one or more segments 224 along flexible body 216 using one or more sensors and/or imaging devices. One catheter/lumen is labeled 222 and includes optical fiber 17. The entire length of flexible body 216, between distal end 218 and proximal end 217, may be effectively divided into segments 224. The tracking system 230 may be implemented as hardware, firmware, software or a combination thereof which interact with or are otherwise executed by one or more computer processors.

The OFDR system 10 and tracking system 230 track the bend of the distal end 218 and/or one or more of the segments 224 using a sensing fiber 17 contained in catheter/lumen 222. In one example embodiment, the sensing fiber has a diameter of approximately 200 μm. In other embodiments, the dimensions may be larger or smaller. The sensing fiber forms a fiber optic bend sensor that the OFDR system 10 measures as described above and provides feedback about the amount of bend at the distal end 218 to the tracking system 230. The tracking system 230 uses the bend data to control the motor drive unit 204 to position pull wires in the fiber. Because accurate control of the tip 218 of the catheter/lumen depends on accurate bend data from the OFDR system 10, any inaccurate data from the bend sensing fiber/OFDR system should be flagged as inaccurate or unreliable so that the tracking system 230 can make correct decisions about the current OFDR data rather than moving the tip 218 to an incorrect location. The redundant core technology described above ensures accurate and reliable feedback.

Flexible body 216 includes a channel 226 sized and shaped to receive a medical instrument. In some embodiments, medical instrument may be used for procedures such as surgery, biopsy, ablation, illumination, irrigation, or suction. The medical instrument may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like.

The medical instrument channel 226 may additionally house cables, linkages, or other actuation controls (not shown) that extend between its proximal and distal ends to controllably adjust the bend distal end of medical instrument. Steerable instruments are described in detail in U.S. Pat. No. 7,316,681 and U.S. patent application Ser. No. 12/286,644, which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable catheters are described in detail in U.S. patent application Ser. No. 13/274,208, which is incorporated by reference herein in its entirety. In embodiments in which medical instrument system 200 is actuated by a teleoperational assembly 234, drive unit 204 may include drive inputs that removably couple to and receive power from drive elements, such as actuators, of the teleoperational assembly. The drive unit 204 and tracking system 230 form a drive unit control loop that uses bend data measured by the OFDR system 10 from the fiber 17 to determine the current position, orientation, shape, etc. of the tip 218 of the catheter (e.g., the tip might be bent 30 degrees left and 10 degrees up). The drive unit control loop receives a command, e.g., from a user like a surgeon, to move the tip 218 to a new position and uses the difference between the tip's current position determined by the OFDR measurements and the commanded position to determine which control wires to actuate by drive unit 204 to move the catheter tip 218 to the commanded position. The drive unit control loop monitors the bend data from the fiber 17/OFDR system 10 to ensure correct motion to the commanded position as the pull wires are manipulated by drive unit 204.

In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

The information from the OFDR system 10 and the tracking system 230 may be sent to a navigation system 232 where it may be combined with information from visualization system 231 and/or the preoperatively obtained models to provide the physician, clinician, or surgeon or other operator with real-time position information. In some examples, the real-time position information may be displayed on display system 233 for use in the control of medical instrument system 200. In some examples, control system 116 of FIG. 1 may utilize position information from the fiber as measured by the OFDR system 10 as feedback for positioning medical instrument system 200. Various systems for using fiber optic sensors to register and display a surgical instrument with surgical images are provided in U.S. patent application Ser. No. 13/107,562, filed May 13, 2011," which is incorporated by reference herein in its entirety.

The technology described above enables a single bend sensing fiber to be used as a bend encoder for a surgical system where any inaccuracy in the bend output must be detected and reported to the system controller. This technology may be used beyond surgical systems to any systems that require inaccurate bend output to be detected for purposes of safety or correct operation). Using a single bend sensing fiber has several advantages over using a secondary bend encoder to detect inaccurate measurements: it is simpler to design, cheaper to manufacture, and requires less space than multiple encoders. Using a single fiber to perform both primary and redundant measurements may also be more accurate than using multiple encoders since the single fiber is guaranteed to experience the same global bends and strains, whereas multiple encoders exist in distinct spaces within the robot, which may cause them to experience different bends and strains.

Those skilled in the art will appreciate that figures in this application may represent conceptual views of illustrative circuitry or other functional units. Similarly, it will be appreciated that flow charts, state transition diagrams, pseudo-code, and the like typically represent various processes which may be substantially represented in computer-readable medium and so executed by a computer or processor, whether or not such computer or processor is explicitly shown.

The functions of the various illustrated elements may be provided through the use of hardware such as circuit hardware and/or hardware capable of executing software in the form of coded instructions stored on computer-readable medium. Thus, such functions and illustrated functional blocks are to be understood as being either hardware-implemented and/or computer-implemented, and thus, machine-implemented.

In terms of hardware implementation, the functional blocks may include or encompass, without limitation, a digital signal processor (DSP) hardware, a reduced instruction set processor, hardware (e.g., digital or analog) circuitry including but not limited to application specific integrated circuit(s) (ASIC) and/or field programmable gate array(s) (FPGA(s)), and (where appropriate) state machines capable of performing such functions.

In terms of computer implementation, a computer is generally understood to comprise one or more processors or one or more controllers, and the terms computer, processor, and controller may be employed interchangeably. When provided by a computer, processor, or controller, the functions may be provided by a single dedicated computer or processor or controller, by a single shared computer or processor or controller, or by a plurality of individual computers or processors or controllers, some of which may be shared or distributed. Moreover, the term "processor" or "controller" also refers to other hardware capable of performing such functions and/or executing software, such as the example hardware recited above.

Whenever it is described in this document that a given item is present in "some embodiments," "various embodiments," "certain embodiments," "certain example embodiments, "some example embodiments," "an exemplary embodiment," or whenever any other similar language is used, it should be understood that the given item is present in at least one embodiment, though is not necessarily present in all embodiments. Consistent with the foregoing, whenever it is described in this document that an action "may," "can," or "could" be performed, that a feature, element, or component "may," "can," or "could" be included in or is applicable to a given context, that a given item "(may," "can," or "could" possess a given attribute, or whenever any similar phrase involving the term "may," "can," or "could" is used, it should be understood that the given action, feature, element, component, attribute, etc. is present in at least one embodiment, though is not necessarily present in all embodiments. Terms and phrases used in this document, and variations thereof, unless otherwise expressly stated, should be construed as open-ended rather than limiting. As examples of the foregoing: "and/or" includes any and all combinations of one or more of the associated listed items (e.g., a and/or b means a, b, or a and b); the singular forms "a", "an" and "the" should be read as meaning "at least one," "one or more," or the like; the term "example" is used provide examples of the subject under discussion, not an exhaustive or limiting list thereof; the terms "comprise" and "include" (and other conjugations and other variations thereof) specify the presence of the associated listed items but do not preclude the presence or addition of one or more other items; and if an item is described as "optional," such description should not be understood to indicate that other items are also not optional.

As used herein, the term "non-transitory computer-readable storage medium" includes a register, a cache memory, a ROM, a semiconductor memory device (such as a D-RAM, S-RAM, or other RAM), a magnetic medium such as a flash memory, a hard disk, a magneto-optical medium, an optical medium such as a CD-ROM, a DVD, or Blu-Ray Disc, or other type of device for non-transitory electronic data storage. The term "non-transitory computer-readable storage medium" does not include a transitory, propagating electromagnetic signal.

Although various embodiments have been shown and described in detail, the claims are not limited to any particular embodiment or example. The technology fully encompasses other embodiments which may become apparent to those skilled in the art. None of the above description should be read as implying that any particular element, step, range, or function is essential such that it must be included in the claims scope. The scope of patented subject matter is defined only by the claims. The extent of legal protection is defined by the words recited in the claims and their equivalents. All structural and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the technology described, for it to be encompassed by the present claims. No claim is intended to invoke 35 USC § 112(f) unless the words "means for" or "step for" are used. Furthermore, no embodiment, feature, component, or step in this specification is intended to be dedicated to the public regardless of whether the embodiment, feature, component, or step is recited in the claims.

What is claimed is:
1. A measurement system, comprising:
a light source configured to direct light into a plurality of cores of a multi-core optical fiber, each core of the plurality of cores being configured to reflect a portion of the light from a plurality of locations along a length of the multi-core optical fiber to form reflected light;
a processor;
memory coupled to the processor, the memory storing instructions that, when executed by the processor, cause the processor to execute operations, the operations comprising:

determining, based on analyzing the reflected light from a first subset of the plurality of cores, a first measurement of a set of bend angles of the multi-core optical fiber;

determining, based on analyzing the reflected light from a second subset of the plurality of cores, a second measurement of the set of bend angles of the multi-core optical fiber, the first subset differing from the second subset by at least one core;

performing a comparison of a specified threshold to a difference, the difference being between the first measurement and the second measurement;

determining whether the first measurement and the second measurement are unreliable based on the comparison; and providing a signal indicative of whether the first measurement and the second measurement are determined to be unreliable.

2. The measurement system of claim 1, wherein determining whether the first measurement and the second measurement are unreliable based on the comparison comprises:
determining that the first measurement and the second measurement are unreliable in response to the difference exceeding the specified threshold.

3. The measurement system of claim 1, wherein the signal is a fault signal indicating that the first measurement and the second measurement are determined to be unreliable, and wherein providing the signal indicative of whether the first measurement and the second measurement are determined to be unreliable comprises:
providing the fault signal in response to determining that the first measurement and the second measurement are unreliable.

4. The measurement system of claim 3, wherein the operations further comprise, in response to the fault signal:
causing a display of a visual indication that a fault is present.

5. The measurement system of claim 3, wherein the operations further comprise, in response to the fault signal:
causing a generation of an audible alarm to indicate that a fault is present.

6. The measurement system of claim 3, wherein the operations further comprise, in response to the signal indicating that the first measurement and second measurement are determined as unreliable:
halting operation of an actuating system, the actuating system configured to cause movement of the multi-core optical fiber.

7. The measurement system of claim 1, wherein:
the cores of the plurality of cores extend along the length of the optical fiber and are equally spaced apart from a central axis of the multi-core optical fiber; and
the plurality of cores includes at least six cores.

8. The measurement system of claim 1, wherein the first subset of the plurality of cores and the second subset of the plurality of cores each include exactly three cores.

9. The measurement system of claim 1, wherein:
analyzing the reflected light from the first subset of the plurality of cores comprises using optical frequency domain reflectometry; and
analyzing the reflected light from the second subset of the plurality of cores comprises using optical frequency domain reflectometry.

10. The measurement system of claim 1, wherein:
the multi-core optical fiber is inserted in a catheter; and
the operations further comprise:
in response to the first measurement and the second measurement not being determined as unreliable, using at least one of the first or second measurements for causing movement of the catheter to a particular shape or to a particular location.

11. A method, comprising:
directing light into a plurality of cores of a multi-core optical fiber, each core of the plurality of cores being configured to reflect a portion of the light from a plurality of locations along a length of the multi-core optical fiber to form reflected light;

determining, based on analyzing the reflected light from a first subset of the plurality of cores, a first measurement of a set of bend angles of the multi-core optical fiber;

determining, based on analyzing the reflected light from a second subset of the plurality of cores, a second measurement of the set of bend angles of the multi-core optical fiber, the first subset differing from the second subset by at least one core;

performing a comparison of a specified threshold to a difference, the difference being between the first measurement and the second measurement;

determining whether the first measurement and the second measurement are unreliable based on the comparison; and providing a signal indicative of whether the first measurement and the second measurement are determined to be unreliable.

12. The method of claim 11, wherein determining whether the first measurement and the second measurement are unreliable based on the comparison comprises:
determining that the first measurement and the second measurement are unreliable in response to the difference exceeding the specified threshold.

13. The method of claim 11, wherein the signal is a fault signal indicating that the first measurement and the second measurement are determined to be unreliable, and wherein providing the signal indicative of whether the first measurement and the second measurement are determined to be unreliable comprises:
providing the fault signal in response to determining that the first measurement and the second measurement are unreliable.

14. The method of claim 13, further comprising, in response to the signal indicating that the first measurement and the second measurement are determined to be unreliable:
causing a display of a visual indication that a fault is present; or
causing a generation of an audible alarm to indicate that a fault is present.

15. The method of claim 13, further comprising, in response to the signal indicating that the first measurement and the second measurement are determined to be unreliable:
halting operation of an actuating system, the actuating system configured to cause movement of the multi-core optical fiber.

16. The method of claim 11, wherein the first subset of the plurality of cores and the second subset of the plurality of cores each include exactly three cores.

17. The method of claim 11, wherein:
the multi-core optical fiber is inserted in a catheter; and
the method further comprises, in response to the first measurement and the second measurement not being determined as unreliable:

using at least one of the first and second measurements for causing movement of the catheter to a particular shape or to a particular location.

18. A non-transitory computer-readable medium storing instructions that, when executed by a processor of a measurement system, the measurement system comprising a light source, cause the processor to execute operations, the operations comprising:
    operating the light source to direct light into a plurality of cores of a multi-core optical fiber, each core of the plurality of cores being configured to reflect a portion of the light from a plurality of locations along a length of the multi-core optical fiber to form reflected light;
    determining, based on analyzing the reflected light from a first subset of the plurality of cores, a first measurement of a set of bend angles of the multi-core optical fiber;
    determining, based on analyzing the reflected light from a second subset of the plurality of cores, a second measurement of the set of bend angles of the multi-core optical fiber, the first subset differing from the second subset by at least one core;
    performing a comparison of a specified threshold to a difference, the difference being between the first measurement and the second measurement;
    determining whether the first measurement and the second measurement are unreliable based on the comparison; and
    providing a signal indicative of whether the first measurement and the second measurement are determined to be unreliable.

19. The non-transitory computer-readable medium of claim 18, wherein determining whether the first measurement and the second measurement are unreliable based on the comparison comprises:
    determining that the first measurement and the second measurement are unreliable in response to the difference exceeding the specified threshold.

20. The non-transitory computer-readable medium of claim 18,
    wherein the signal is a fault signal indicating that the first measurement and second measurement are determined to be unreliable,
    wherein providing the signal indicating whether the first measurement and the second measurement are determined to be unreliable comprises:
    providing the fault signal in response to the determination that the first measurement and the second measurement are unreliable; and
    wherein the operations further comprise, in response to the fault signal, at least one of: causing a display of a visual indication that a fault is present;
    halting operation of an actuating system that is configured to cause movement of the multi-core optical fiber; or
    causing a generation of an audible alarm to indicate that a fault is present.

* * * * *